United States Patent [19]

Marty et al.

[11] Patent Number: 4,895,952

[45] Date of Patent: Jan. 23, 1990

[54] POLYFLUOROALKYLTHIOMETHYL COMPOUNDS, PROCESSES FOR THEIR PREPARATION AND USE THEREOF

[75] Inventors: Frederique Marty, Nice; Emile Rouvier, Tourrette-Le-Vens; Aime Cambon, Nice, all of France

[73] Assignee: Atochem, Paris, France

[21] Appl. No.: 946,822

[22] Filed: Dec. 29, 1986

[30] Foreign Application Priority Data

Jan. 7, 1986 [FR] France ................ 86 00135

[51] Int. Cl.$^4$ .......................................... C07D 213/32
[52] U.S. Cl. .................................. 546/339; 568/11; 568/56; 568/39
[58] Field of Search ............. 526/243; 568/11, 40, 568/55, 39, 56; 546/339; 252/545, 135

[56] References Cited

U.S. PATENT DOCUMENTS

| | | | |
|---|---|---|---|
| 3,172,910 | 3/1965 | Brace | 562/605 |
| 3,655,732 | 4/1972 | Rondestvedt | 560/22 |
| 4,296,034 | 10/1981 | Bouvet et al. | 252/545 |

FOREIGN PATENT DOCUMENTS

| | | | |
|---|---|---|---|
| 764455 | 3/1970 | Belgium | 252/545 |
| 1221216 | 7/1964 | Fed. Rep. of Germany | 568/55 |

OTHER PUBLICATIONS

English–Language Derwent Abstract of French Patent 2,516,920, Accession Number 83-61806K/26 Cambon et al.

Roberts & Caserio, *Basic Principles of Organic Chemistry*, 2nd. ed., 1977, p. 214.

*Primary Examiner*—John Doll
*Assistant Examiner*—Stuart L. Hendrickson
*Attorney, Agent, or Firm*—Sigalos, Levine & Montgomery

[57] ABSTRACT

A polyfluoroalkylthiomethyl compound of the formula:

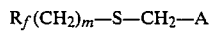

$$R_f(CH_2)_m-S-CH_2-A$$

in which $R_f$ is a straight-chain or branched perfluoroalkyl radical containing from 2 to 16 carbon atoms, m is an integer from 1 to 4, and A is a hydroxyl group, a chlorine or bromine atom, an ammonium group derived from a secondary or tertiary amine, a phosphonium group, or an ionic or nonionic group $-Q-(CH_2)_n-Z$, in which Q is an oxygen or sulphur atom, n the number 0, 1 or 2, and Z an unsubstituted or substituted alkyl, aryl or alkylaryl radical. The invention also comprises the method of making such compound and the use thereof as a surface-active agent.

9 Claims, No Drawings

POLYFLUOROALKYLTHIOMETHYL COMPOUNDS, PROCESSES FOR THEIR PREPARATION AND USE THEREOF

BACKGROUND OF THE INVENTION

The present invention relates to new polyfluoro compounds and, more particularly, polyfluoroalcohols of the hemithioacetal type, which form valuable intermediates for the synthesis of polyfluoro derivatives, especially ionic surface-active agents.

In U.S. Pat. No. 3,655,732, which relates, inter alia, to acrylic monomers of general formula:

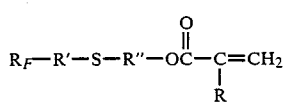

in which R is a halogen atom or a methyl radical, $R_F$ denotes a perfluoralkyl radical and R' and R'' denote alkylene bridges, it is indicated (column 4, lines 63–72) that the hemithioacetals of formula:

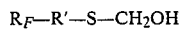

are not accessible by the known methods. Since the corresponding acrylic monomers:

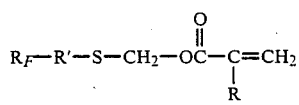

cannot therefore be obtained by direct esterification, it is proposed in the abovementioned patent to prepare these monomers indirectly by reacting a thiol $R_F$—R'—SH with formaldehyde and hydrochloric acid to form a chloromethyl derivative $R_F$—R'—S—CH$_2$Cl which is then reacted with sodium acrylate or methacrylate; the operating conditions are not given. Furthermore, according to the literature (H. Bohme, Chem. Ber. 69, 1610; patent DE 845,511; H. Bohme et al., Ann. 563, 54), the reaction of a thiol with formaldehyde and hydrochloric acid must be carried out at very low temperature (from −15° to −5° C.). It has been found, however, that when it is applied to fluorothiols $R_F$—R'—SH, this reaction does not yield chloromethyl derivatives, but thioacetals $(R_F$—R'—S$)_2$ CH$_2$.

SUMMARY OF THE INVENTION

It has now been found that the hemithioacetals (II) may be obtained by the reaction of trioxymethylene (of s-trioxane) with a polyfluoroalkanethiol. In addition, by starting with these new polyfluoroalchols it has been possible to prepare various derivatives which can be used as surface-active agents or precursors thereof.

Generally therefore, the subject of the invention are polyfluoroalkylthiomethyl compounds of general formula:

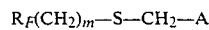

in which $R_F$ is a straight-chain or branched perfluoralkyl radical containing from 2 to 16 carbon atoms, m is an integer from 1 to 4, preferably equal to 2, and A is a hydroxyl group, a chlorine or bromine atom, an ammonium group derived from a secondary or tertiary amine, a phosphonium group, or an ionic or nonionic group —Q—(CH$_2$)$_n$—Z, in which Q is an oxygen or sulphur atom, n the number 0, 1 or 2, and Z an alkyl, aryl or alkylaryl radical, substituted if desired.

The invention also comprises the method of making such compounds and their use as hereinafter set forth.

DETAILED DESCRIPTION

Among these compounds preference is given to those in which the perfluoroalkyl radical $R_F$ is straight-chain and contains 4, 6, 8 or 10 carbon atoms.

When A denotes an ammonium group, the latter is preferably chosen from those of formulae:

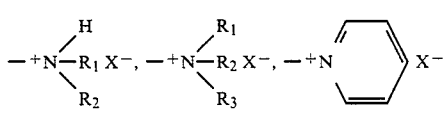

and

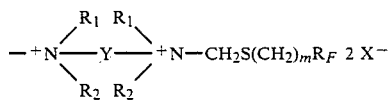

in which $R_1$, $R_2$ and $R_3$ may be identical or different and each is an alkyl, phenyl or benzyl radical, substituted if desired, Y denotes an alkylene bridge containing 2 to 6 carbon atoms, interrupted by an oxygen atom if desired, and $X^-$ denotes a monovalent anion or its equivalent. The alkyl radical may be straight-chain or branched and may contain from 1 to 18 carbon atoms. As substituents which, if desired, are present on the alkyl, phenyl and benzyl radicals there may be mentioned the halogen atoms, hydroxyl and nitrile groups, and ester, acid, sulphonate, sulphate or carboxylate functional groups.

The phosphonium group which A may denote is preferably a group of formula:

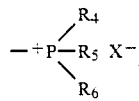

in which the symbols $R_4$, $R_5$ and $R_6$ may be identical or different and each denotes an alkyl or aryl (especially phenyl) radical, $X^-$ having the same meaning as above. The alkyl radicals may contain from 1 to 6 carbon atoms.

When A is a —Q—(CH$_2$)$_n$—Z group, the alkyl, aryl or alkylaryl radical Z may carry hydrophilic substituents, ionic or non-ionic, such as hydroxyl, alkoxycarbonyl (for example methoxycarbonyl or ethoxycarbonyl), aryloxycarbonyl (for example phenoxycarbonyl), ammonium, carboxylate, betaine, sulphonate, sulphate or phosphate groups, and/or nonhydrophilic substituents such as halogen atoms or nitrile, acyl (for example acetyl or benzoyl) or dialkylamino (C$_1$-C$_4$ alkyl) groups.

To prepare the compounds of formula (IV) in which A is a hydroxyl group, that is to say, the alcohols of formula:

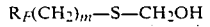

trioxymethylene is reacted with a polyfluoroalkanethiol $R_F$(CH$_2$)$_m$—SH, in a proportion of three moles of thiol per one mole of trioxymethylene. The reaction is carried out in the presence of a tertiary amine as a catalyst, in a proportion of $2 \times 10^{-4}$ to $2 \times 10^{-1}$ mole per mole of trioxymethylene. This tertiary amine is preferably triethylamine, but it is also possible to use other amines such as, for example tripropylamine, tributylamine, dimethylethylamine, dimethylcyclohexylamine, dimethylaniline, N-methylpiperidine and pyridine, as well as quaternary ammonium hydroxides such as trimethylbenzylammonium hydroxide (Triton B). The polyfluoroalkanethiols employed as starting materials are well-known compounds (see, for example, patents U.S. No. 2,894,991, U.S. No. 3,088,849, U.S. No. 3,544,663, FR 1,221,415 and FR 2,083,422).

The reaction may be carried out at a temperature of up to 50° C., optionally in an inert organic solvent (for example an ether or a halogenated hydrocarbon). However, in order to avoid the concurrent formation of the disulphide $(R_F(CH_2)_mS)_2$ which, despite representing a small proportion, is difficult to separate, it is particularly desirable to operate in the region of about 0° C. under an inert gas atmosphere (particularly nitrogen) and in the absence of solvent. Under these conditions, an alcohol (IV-a) is obtained which is sufficiently pure to be used as such.

In order to synthesize the other compounds of formula (IV) according to the invention, the alcohols (IV-a) are then subjected to a halogenation to form the corresponding chlorides and, preferably, bromides of formula:

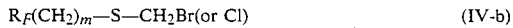

$$R_F(CH_2)_m\text{—S—}CH_2Br(\text{or Cl}) \qquad (\text{IV-b})$$

Phosphorus trichloride or tribromide, phosphorus pentachloride, phosphorus oxychloride or thionyl chloride, for example, may be used as halogenating agents. The halogenation reaction may be carried out at a temperature of up to 80° C. in an inert organic solvent. To avoid the concurrent formation of the thioacetal $[R_F(CH_2)_mCH_2S]_2CH_2$, the operation is preferably performed in the vicinity of 0° C. under an inert gas atmosphere and in an anhydrous ether.

The compounds of formula (IV) in which A is an ammonium group may be prepared by the reaction of an α-halogenated, preferably α-brominated, sulphide (IV-b) with a secondary or tertiary amine.

The reaction is preferably performed by dissolving substantially equimolar quantities of the α-halogenated sulphide (IV-b) and of the chosen amine in two or three volumes of ether. After a short induction period, an exothermic reaction occurs with the formation of a hydrogen halide (in the case of secondary amines) or of a quaternary ammonium halide (in the case of tertiary amines). These salts, which precipitate from the reaction mixture, may then be recrystallized, for example from a mixture of ethyl acetate and chloroform or from acetone. The majority have a crystalline structure and are not hygroscopic; they are all completely soluble in water and form neutral solutions.

As nonlimiting examples of amines which can be used, there may be more particularly mentioned trimethylamine, triethylamine, tripropylamine, triisopropylamine, tributylamine, dimethylethylamine, N,N-dimethylaniline, N,N-dimethylbenzylamine, N,N-dimethylated fatty amines, that is to say N,N-dimethylalkyl amines in which the alkyl radical contains from 8 to 18 carbon atoms (especially N,N-dimethyloctylamine), pyridine, N,N-dimethylethanolamine, N,N-diethylethanolamine, N,N-dibutylethanolamine, N-methyldiethanolamie, triethanolamine, ethyl 3-dimethylaminopropionate, and ethyl methylaminobenzoate. It is also possible to use diamines, provided that a double molar proportion of halogenated sulphide (IV-b) is employed; a typical example of a diamine which can be used is N,N,N',N'-tetramethylethylenediamine, which yields double salts of formula:

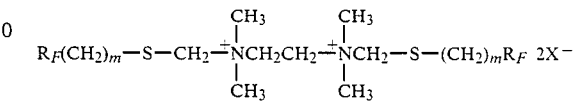

Other examples of diamines are N,N,N',N'-tetramethyl-1,6-hexanediamine and N,N,N',N'-tetramethyl diaminodiethyl ether.

The compounds of formula (IV) in which A is a phosphonium group may be prepared in the same manner as the ammonium salts by replacing the secondary or tertiary amine with a phosphine. Since the reaction takes place more slowly than with the amines, it is desirable to operate under reflux. As examples of phosphines, which can be used, there may be mentioned, without implying any limitation, triphenylphosphine, trimethylphosphine, triethylphosphine and tributylphosphine.

The $Br^-$ or $Cl^-$ anion of the ammonium or phosphonium salts may, if desired, be readily exchanged for another anion using methods which are well known per se. As examples of other anions there may be more specially mentioned the iodide, nitrate, p-toluenesulphonate, sulphate, alkylsulphate and picrate anions.

The ammonium or phosphonium salts of the present invention are valuable surface-active agents which can be used in an effective amount as additives in a wide variety of fields, as wetting agents, emulsifiers, dispersants or foaming agents.

The compounds of formula (IV) in which A is a $-Q-(CH_2)_n-Z$ group may be prepared by the reaction of an α-halogenated sulphide (IV-b) with a sodium alcoholate or thiolate of formula:

$$Na-Q-(CH_2)_n-Z \qquad (V)$$

in which Q, n and Z have the same meanings as above.

This reaction may be carried out at a temperature of up to 80° C. by adding the α-halogenated sulphide (IV-b) to a suspension of the sodium salt (V) in an inert organic solvent; for example, an ether. It is advantageous to use an excess of compound (V), it being possible for this excess to range up to 50%. To avoid the undesirable formation of thioacetal $[R_F(CH_2)_m-S]_2CH_2$, the addition of the α-halogenated sulphide (IV-b) is preferably carried out at 0° C. and under an inert atmosphere, and the reaction may then be completed at ambient temperature, by stirring.

After removal of the insolubles and of the solvent, the compounds of formula:

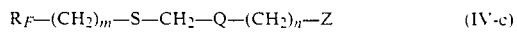

$$R_F-(CH_2)_m-S-CH_2-Q-(CH_2)_n-Z \qquad (IV\text{-}c)$$

may be isolated and, if desired, purified using conventional methods such as distillation under reduced pressure. When Z carries at least one hydrophilic substituent, these compounds can be used as surface-active agents in the same fields as those previously mentioned with relation to the ammonium or phosphonium salts.

When the radical Z is not substituted or is substituted by non-hydrophilic substituents, the compounds (IV-c) constitute valuable intermediates for the preparation of surface-active agents.

The invention will be further described in connection with the following examples which are set forth for purposes of illustration only.

EXAMPLE 1

3.16 g (0.035 mole) of trioxymethylene and 10 drops of triethylamine are introduced into a 200 ml round-bottomed flask fitted with a magnetic stirrer and a dropping funnel containing 40 g (0.105 mole) of 2-perfluorohexylethanethiol ($C_6F_{13}C_2H_4SH$). The flask is cooled with an iced water bath and the mixture is placed under a nitrogen atmosphere.

Slow addition of the thiol is then commenced, while the temperature of the reaction mixture is maintained at 0° C. until the trioxymethylene has been consumed. The reaction mixture, which is then in the form of a bluish, still slightly opaque solution, is then returned to ambient temperature and kept stirred for 24 hours.

Water is then added to the clear solution obtained in this manner and extraction with ethyl ether is carried out. The ether phase is then washed several times with water and is then dried over sodium sulphate. After filtration and removal of the ether, (2-perfluorohexylethylthio)methanol, $C_6F_{13}C_2H_4SCH_2OH$, is then obtained in a 90–95% yield, in the form of a colorless liquid with a characteristic odor. B.p.: 67°–69° C. (6666 Pa).

By proceeding in the same manner and starting with the thiols: $C_4F_9C_2H_4SH$ and $C_8F_{17}C_2H_4SH$, the following alcohols are obtained, respectively:

$C_4F_9C_2H_4SCH_2OH$ ... B.p.=48°–52° C. (5333 Pa).
$C_8F_{17}C_2H_4SCH_2OH$ ... M.P.=20° C.

EXAMPLE 2

In a round-bottomed flask supporting a condenser and a dropping funnel, cooled in an ice bath and placed under a nitrogen atmosphere, 44 g (0.107 mole) of the alcohol ($C_6F_{13}C_2H_4SCH_2OH$) are introduced into 50 ml of anhydrous ethyl ether. 10 ml of phosphorus tribromide (0.107 mole) dissolved in 50 ml of anhydrous ethyl ether are then added dropwise via the dropping funnel. When the addition is complete, the iced water bath is removed and the reaction is completed by continuing the stirring for 12 hours at ambient temperature.

The reaction mixture is then poured into iced water and is then extracted with ether. The ether phase is then washed with a dilute (0.05%) sodium hydroxide solution, and then several times with water. After drying over sodium sulphate, filtering and evaporating the ether, a distillation under reduced pressure enables 2-perfluorohexylethylthiomethyl bromide $C_6F_{13}C_2H_4SCH_2Br$ to be obtained. B.p.=124° C. (6666 Pa). Yield: 93%.

By proceeding in the same manner and starting from (2-perfluorobutylethylthio)methanol, 2-perfluorobutylethylthiomethyl bromide $C_4F_9C_2H_4SCH_2Br$, which boils at 98° C. at 5333 Pa, is obtained in a 90% yield.

EXAMPLE 3

The procedure followed is as in Example 2, but with phosphorus tribromide replaced with an equimolar quantity of thionyl chloride and with the use of chloroform as solvent (5 ml per gram of $R_FC_2H_4SCH_2OH$).

The following chlorine compounds are obtained in a yield of 65 to 70%:

$C_6F_{13}C_2H_4SCH_2Cl$ ... B.p.=114° C. (8000 Pa).
$C_4F_9C_2H_4SCH_2Cl$ ... B.p.=90° C. (6666 Pa).

EXAMPLE 4

The salts of formula:

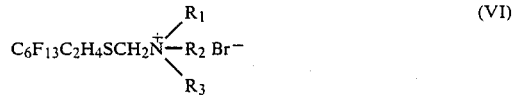

were prepared from the amines $NR_1R_2R_3$ listed in the first column of Table 1 below, using the following procedure:

Equimolar quantities of the α-brominated sulphide: $C_6F_{13}C_2H_4SCH_2Br$ and of amine $NR_1R_2R_3$ dissolved in two or three volumes of ethyl ether are introduced into a round flask fitted with a magnetic stirrer. The reaction is exothermic and virtually instantaneous. The quaternary salt precipitates in the form of a white solid. Stirring is continued until the α-brominated sulphide has been completely consumed, and then the solid obtained is thoroughly rinsed with ether and is then recrystallized by being dissolved in a hot mixture of ethyl acetate (5 ml per gram of solid) containing sufficient chloroform to form a clear solution; after cooling and filtration, the corresponding quaternary salts of formula (VI) are obtained. These salts, identified by NMR, IR and mass spectrometry, are completely soluble in water. Their melting points and the surface tension at 25° C. of a 0.1% strength aqueous solution are shown in the third and fourth columns of Table I below, the second column indicating the yield.

EXAMPLE 5

The procedure is as in Example 4, N,N,N',N'-tetramethylethylenediamine being used as the amine in a sulphide/amine molar ratio of 2. The double quaternary salt of formula:

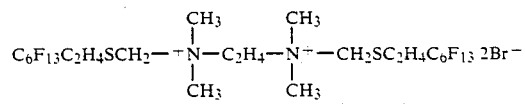

which melts at 164°–165° C., is obtained in this manner in an 81% yield. The surface tension of a 0.1% strength aqueous solution of this salt is 14.9 mN/m at 25° C.

TABLE I

| | Salt of formula (VI) | | |
|---|---|---|---|
| Amine $NR_1R_2R_3$ | Yield (in %) | Melting point (in °C.) | Surface tension (in mN/m) |
| N,N—dimethylaniline | 87 | 92–93 | 17.5 |
| Pyridine | 82 | 137–138 | 22.7 |
| Triethylamine | 80 | | 29.9 |
| N,N—dimethylbenzylamine | 88 | 143 | 17.5 |
| N,N—dimethyloctylamine | 73 | 175 | 15.5 |
| N,N—dimethylethanolamine | 93 | 74–76 | 23.1 |
| N,N—dibutylethanolamine | 66 | 85–86 | 17.8 |
| N—methyldiethanolamine | 84 | 185 | 16.2 |
| Ethyl 3-dimethylaminopropionate | 92 | 106–108 | 22.8 |

EXAMPLE 6

2 g (5.36 mmol) of the bromide $C_4F_9C_2H_4SCH_2Br$ and 1.82 g (6.97 mmol) of triphenylphosphine dissolved in 20 ml of anhydrous ethyl ether are introduced into a 50 ml round-bottomed flask fitted with a condenser, and are then heated under reflux for 48 hours, with stirring. A white precipitate forms and is filtered through sintered glass, rinsed thoroughly with ether and then recrystallized from ethyl acetate.

The salt of formula:

$$C_4F_2H_4SCH_2{}^+P(C_6H_5)_3Br^-$$

identified by NMR and IR spectrometry and by elemental analysis, is obtained in this manner.

EXAMPLE 7

1.09 g (8.24 mmol) of sodium thiophenate suspended in 30 ml of anhydrous ethyl ether are introduced into a round-bottomed flask supporting a condenser and a dropping funnel, cooled in an ice bath and placed under inert atmosphere. A solution of 3 g (6.34 mmol) of $C_6F_{13}C_2H_4SCH_2Br$ in 20 ml of ether is then added dropwise via the dropping funnel.

After the addition, the ice bath is removed and the reaction is completed by continuing the stirring for 24 hours at ambient temperature. The reaction mixture is then filtered through sintered glass and the residue (excess sodium thiophenate and sodium bromide formed in situ) is rinsed with ether. After the filtrate has been collected, the ether is removed by evaporation and a distillation under reduced pressure is then carried out.

A yield in the region of 100% of the compound $C_6F_{13}C_2H_4SCH_2SC_6H_5$, which boils at 162° C. at 5333 Pa and which has been identified by NMR, IR and mass spectrometry, is obtained in this manner.

When sodium thiophenate is replaced with the sodium salt of benzylmercaptan or of methyl thioglycolate, the following compounds are obtained, respectively:

$C_6F_{13}C_2H_4SCH_2SCH_2C_6H_5$ . . . B.p.=183° C. (5333 Pa).

$C_6F_{13}C_2H_4SCH_2sch_2CO_2CH_3$ . . . B.p.=191° C. (8000 Pa).

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A polyfluoroalkylthiomethyl compound of the formula:

$$R_F(CH_2)_m—S—CH_2—A$$

in which $R_F$ is a straight-chain or branched perfluoroalkyl radical containing from 2 to 16 carbon atoms, m is an integer from 1 to 4, and A is an ammonium group derived from a secondary or tertiary amine, a phosphonium group, or an ionic or nonionic group —Q—(CH$_2$)$_n$—Z, in which Q is an oxygen or sulphur atom, n the number 0, 1 or 2, and Z an unsubstituted alkyl, aryl or alkylaryl radical.

2. The compound of claim 1, in which m is equal to 2.

3. The compound of claim 1, in which A is an ammonium group selected from:

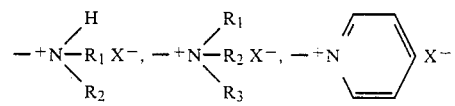

and

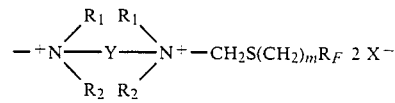

in which $R_1$, $R_2$ and $R_3$ can be the same or different and each is an unsubstituted alkyl, phenyl or benzyl radical, Y is a $C_2$ to $C_6$ alkylene bridge or a $C_2$ to $C_6$ alkylene bridge interrupted by an oxygen atom, and $X^-$ is an anion or anions necessary to balance the charge.

4. The compound of claim 3, wherein at least one of the radicals $R_1$, $R_2$ and $R_3$ is substituted by a halogen atom, a hydroxyl group, a nitrile group, an ester, acid, sulphonate, sulphate, or carboxylate functional group.

5. The compound of claim 1 or 2, in which A is a phosphonium group:

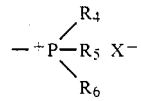

in which $R_4$, $R_5$ and $R_6$ can be the same or different and each is an alkyl or aryl radicl and $X^-$ is an anion or anions necessary to balance the charge.

6. A polyfluoroalkylthiomethyl compound of the formula:

$$R_F(CH_2)_m—S—CH_2—A$$

in which $R_F$ is a straight-chain or branched perfluoroalkyl radical containing from 2 to 16 carbon atoms, m is an integer from 1 to 4, and A is a chlorine or bromine atom.

7. The compound of claim 6, in which m is equal to 2.

8. A process for the preparation of a polyfluoroalkylthiomethyl compound of claim 1 in which A is a hydroxyl group comprising reacting trioxymethylene with a polyfluoroalkanethiol; $R_F(CH_2)_m$—SH, in a proportion of three moles of thiol per one mole of trioxymethylene.

9. The process of claim 8, in which the reaction is carried out at a temperature of about 0° C. under an inert gas atmosphere and in the absence of solvent.

* * * * *